United States Patent
Sass (10) Patent No.: US 9,594,076 B2
(45) Date of Patent: Mar. 14, 2017

(54) METHOD FOR DETERMINING LIPIDS AND OTHER INTERFERING SUBSTANCES IN BODY FLUID SAMPLES

(71) Applicant: Siemens Healthcare Diagnostics Products GmbH, Marburg (DE)

(72) Inventor: Karl Sass, Kirchhain (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

(21) Appl. No.: 15/005,850

(22) Filed: Jan. 25, 2016

(65) Prior Publication Data

US 2016/0216249 A1 Jul. 28, 2016

(30) Foreign Application Priority Data

Jan. 27, 2015 (EP) ..................................... 15152606

(51) Int. Cl.
| G01N 21/00 | (2006.01) |
| G01N 33/00 | (2006.01) |
| G01N 33/49 | (2006.01) |
| G01N 21/31 | (2006.01) |
| G01N 21/27 | (2006.01) |

(52) U.S. Cl.
CPC .......... *G01N 33/492* (2013.01); *G01N 21/274* (2013.01); *G01N 21/314* (2013.01); *G01N 21/3151* (2013.01); *G01N 2201/06146* (2013.01)

(58) Field of Classification Search
USPC ................................................. 356/432–444
See application file for complete search history.

(56) References Cited

U.S. PATENT DOCUMENTS

| 3,569,721 A * | 3/1971 | Goldberg ............ G01N 21/314 250/226 |
| 4,263,512 A * | 4/1981 | Sagusa .................... G01J 3/427 250/373 |
| 4,663,530 A * | 5/1987 | Shields ................. G01N 33/06 250/339.12 |
| 6,882,425 B1 * | 4/2005 | Elsenhans ............ G01N 21/274 356/40 |
| 2009/0009750 A1 * | 1/2009 | Johansson ............ G01N 21/314 356/39 |
| 2010/0174491 A1 * | 7/2010 | Kim ..................... G01N 33/728 702/19 |
| 2014/0192342 A1 | 7/2014 | Sass et al. |

FOREIGN PATENT DOCUMENTS

| EP | 1059522 A1 | 12/2000 |
| WO | WO 2006040387 A1 | 4/2006 |
| WO | WO 2013010970 A1 | 1/2013 |

OTHER PUBLICATIONS

European Search Report of European Application No. 15152606. 8-1553 mailed Aug. 21, 2105.

* cited by examiner

*Primary Examiner* — Tri Ton
*Assistant Examiner* — Jarreas C Underwood
(74) *Attorney, Agent, or Firm* — Dugan & Dugan, PC (57) ABSTRACT

The present invention relates to a method and an automatic analyzer for determining more accurately the concentration of lipids and other interfering substances in body fluids, particularly of interfering substances such as bilirubin and hemoglobin in blood serum and blood plasma samples.

16 Claims, 5 Drawing Sheets

METHOD FOR DETERMINING LIPIDS AND OTHER INTERFERING SUBSTANCES IN BODY FLUID SAMPLES

CROSS REFERENCE TO RELATED APPLICATION

This claims priority to European Patent Application No. EP 15152606.8, filed Jan. 27, 2015, which is hereby incorporated by reference herein in its entirety for all purposes.

FIELD

The present invention relates to a method and an automatic analyzer for determining the concentration of lipids and other interfering substances in body fluids, particularly of interfering substances such as bilirubin and hemoglobin in blood serum and blood plasma samples.

BACKGROUND

Numerous detection and analysis methods for determining physiological parameters in body fluid samples are based on photometric measuring principles. Photometric methods allow the qualitative and quantitative detection of analytes in liquid samples.

In many cases, clinically relevant parameters, examples including the concentration or the activity of an analyte, are determined by mixing an aliquot of a body fluid from a patient with one or more assay reagents in vitro, initiating a biochemical reaction which brings about a measurable change in an optical property of the assay preparation. Photometry examines and utilizes the attenuation of a luminous flux upon penetration through an absorbing and/or scattering medium. Different photometric measurement methods allowing the measurement of a turbid liquid assay preparation are used depending on the nature of the triggered biochemical or biophysical reaction.

To this end, it is possible to use turbidimetric methods, in which the turbidity or the optical density of a solution or suspension is measured on the basis of the light attenuation or absorbance of a light beam passing directly through the suspension.

The intensity of the light beam decreases upon penetration through a measurement cell or cuvette containing a liquid sample. The losses can be influenced by interactions of the light beam with the sample situated in the measurement cell, for example by absorption, diffraction, scattering and/or reflection effects. It is generally possible for diffraction, scattering and reflection effects to be disregarded or compensated for by reference measurements, so that mainly absorption contributes to the attenuation of the light beam.

Photometric determinations of concentration are therefore based on a law where the absorbance or absorption is dependent on the concentration of the dissolved substances and the layer thickness of the measurement cell at a certain wavelength of the incident light. This relationship is described by the Beer-Lambert law:

$$E(\lambda) = -\log(I/I_0) = \epsilon(\lambda) \cdot c \cdot d$$

where $E(\lambda)$ is the absorbance dependent on the wavelength $\lambda$ of the light beam, $I$ is the light intensity after penetration through the sample, $I_0$ is the light intensity before penetration through the sample, $\epsilon(\lambda)$ is the wavelength-dependent molar extinction coefficient of a transirradiated substance, $c$ is the molar concentration of the transirradiated substance, and $d$ is the layer thickness transirradiated by the light beam, for example of the measurement cell.

On the basis of the absorbance $E(\lambda)$ of a sample, it is possible to ascertain the concentration of a substance in a solution. To this end, it is necessary for the absorbance of at least one standard solution of known concentration to have been determined beforehand. Since absorbance is proportional to concentration, it is possible to ascertain the concentration of a dissolved substance in an unknown sample by means of calibration by absorbance measurements of multiple standard solutions of known concentrations.

However, the absorbance of a sample depends not only on the concentration of the substance to be determined itself, but also on the nature of the sample matrix. The absorbances of various substances are additive in a mixture, if the substances do not interact with one another. Body fluids, examples including blood plasma or blood serum, are complex mixtures and contain not only the analyte to be determined, but also a multiplicity of further substances which influence the total absorption of the sample.

However, in individual cases, body fluid samples may contain abnormally high concentrations of one or more intrinsic, i.e., endogenous, substances which turn out to be interfering in photometric detection methods when a tolerable concentration is exceeded and may have an effect in relation to a systematic error.

It is known that problems are caused by hemolytic, icteric and/or lipemic serum or plasma samples, which have abnormally high hemoglobin, bilirubin and/or lipid concentrations. Abnormally high concentrations of these interfering substances may be caused by a pathological state of the patient or else by an improper acquisition or storage of sample. If such samples are subjected to a photometric method used for determining an analytical, diagnostically relevant parameter, there is the risk of an incorrect determination, the result of which may be possibly a misdiagnosis and, in the worst case, an incorrect treatment of the patient. The preanalytical identification of hemolytic, icteric and lipemic samples is thus particularly important for avoiding faulty analysis results.

Therefore, there is a need for methods for ascertaining the spectrometric effects of interfering substances in body fluid samples or for identifying body fluid samples containing elevated concentrations of one or more interfering substances.

EP-A1-1059522, U.S. Pat. No. 4,263,512, US 2009/0009750 A1 and US 2010/0174491 A1 describe various methods for determining bilirubin, hemoglobin and lipids in plasma or serum samples. For example, in EP-A1-1059522, the absorbance which remains after subtraction of the absorbance due to hemoglobin and bilirubin and which contains in particular the absorbance caused by lipids is subjected to local linear approximation.

However, even the last-mentioned method has the disadvantage that specifically a comparatively high lipid concentration may influence the determination of bilirubin and hemoglobin in the same sample and thus distort the measurement values.

WO 2013/010970 A1 already describes a method which allows, even in the presence of high lipid concentrations, an accurate determination of bilirubin and hemoglobin and also a determination of lipid concentration in one sample. The method described in WO 2013/010970 A1 fundamentally comprises the measurement of the absorbance of the sample at various wavelengths, the calculation of a power-function approximation curve for the absorbance of the lipids, the subtraction of the hemoglobin and bilirubin share of the absorbances until a lipid curve remains, and lastly—for determining the lipid content—the division of a thus theoretically ascertained lipid absorbance value by the extinction coefficient specific for lipids.

With the known method, it has been observed that it is possible to correctly determine the lipid content in only approximately 20% of all samples. In the case of the remaining samples, the determined lipid content deviates from the true lipid content by more than +/−25%.

SUMMARY

It is therefore an object of the present invention to modify the method according to WO 2013/010970 A1 in such a way that it allows a more accurate determination of the lipid concentration in body fluid samples.

This object is achieved, inter alia, by the fact that, according to the invention, instead of a lipid absorbance value theoretically ascertained at a lipid-specific wavelength being divided by the extinction coefficient specific for lipids, the difference between two values of the approximation curve for the absorbance of the lipids at two different wavelengths is generated and is divided by the extinction coefficient specific for lipids.

This approach allows a substantially more accurate determination of the lipid concentration in body fluid samples. What is achieved is that the lipid content determined using the method according to the invention does not deviate in any case by more than +/−20% from the true lipid content. Thus, the method according to the invention achieves an accuracy of lipid determination that is comparable to the accuracy of a chemical analysis, but with the additional advantage that it is not necessary in the method according to the invention to mix any reagents with the sample.

The present invention therefore provides a method for determining the concentration of lipids in a body fluid sample, comprising the steps:

a) transirradiating the body fluid sample with light at a multiplicity of wavelengths;

b) capturing a first measurement value (A1) at a first wavelength at which the absorbance not caused by lipids is negligible;

c) capturing a second measurement value (A2) at a second wavelength at which bilirubin has an absorbance maximum;

d) capturing a third measurement value (A3) at a third wavelength at which hemoglobin has an absorbance maximum;

e) capturing a fourth measurement value (A4) at a fourth wavelength at which the absorbance not caused by bilirubin and hemoglobin and lipids is negligible;

f) calculating a power-function approximation curve ($L_0$) of the form $$E(\lambda) = p_0 \cdot \lambda^{q_0}$$

for the absorbance of the lipids on the basis of the first measurement value (A1) by determining the factor $p_0$ at predetermined exponent $q_0$;

g) determining an approximation value of the bilirubin concentration ($c_B$) on the basis of a first theoretical absorbance value ($E_B$) for bilirubin, corresponding to the difference between the second measurement value (A2) and the value of the approximation curve ($L_0$) at the second wavelength;

h) determining an approximation value of the hemoglobin concentration ($c_H$) on the basis of a second theoretical absorbance value ($E_H$) for hemoglobin, corresponding to the difference between the third measurement value (A3) and the value of the approximation curve ($L_0$) at the third wavelength;

i) determining a third theoretical absorbance value ($E_{HBL}$) for the fourth wavelength on the basis of the sum of the theoretical absorbance values for hemoglobin ($E_H$) and bilirubin ($E_B$) and the value of the approximation curve ($L_0$) at the fourth wavelength;

j) ascertaining a deviation of the third theoretical absorbance value ($E_{HBL}$) from the fourth measurement value (A4), wherein I.—if the deviation ascertained in step j) does not exceed a predetermined threshold value—the concentration ($c_L$) of lipids is determined by generating the difference between the value of the approximation curve ($L_0$) at the fourth wavelength and the value of the approximation curve ($L_0$) at the first wavelength and dividing said difference by the extinction coefficient specific for lipids, or II.—if the deviation ascertained in step j) exceeds a predetermined threshold value—a corrected approximation curve ($L_k$) for the absorbance of the lipids is calculated and steps g) to j) are repeated with the values of the corrected approximation curve ($L_k$) until the deviation reaches or falls short of the predetermined threshold value, and the concentration ($c_L$) of lipids is determined by i.—if the first measurement value (A1) does not exceed a predetermined absorbance threshold value for the absorbance at the first wavelength—generating the difference between the value of the corrected approximation curve ($L_k$) at the fourth wavelength and the value of the approximation curve ($L_k$) at the first wavelength and dividing said difference by the extinction coefficient specific for lipids or ii.—if the first measurement value (A1) exceeds a predetermined absorbance threshold value for the absorbance at the first wavelength and if the exponent $q_k$ of the corrected approximation curve is greater than —1— correcting the value of the corrected approximation curve ($L_k$) at the first wavelength by means of an equalizing function which relates the first measurement value (A1) to the value of the corrected approximation curve ($L_k$) at the first wavelength, and then generating the difference between the value of the corrected approximation curve ($L_k$) at the fourth wavelength and the value at the first wavelength, as corrected by application of the equalizing function, and dividing said difference by the extinction coefficient specific for lipids.

In one embodiment of the method according to the invention, the first wavelength at which the absorbance not caused by lipids is negligible is between 600 nm and 660 nm; preferably, it is 645 nm.

In a further embodiment of the method according to the invention, the second wavelength at which bilirubin has an absorbance maximum is between 440 nm and 480 nm; preferably, it is 470 nm.

In again a further embodiment of the method according to the invention, the third wavelength at which hemoglobin has an absorbance maximum is between 400 nm and 440 nm; preferably, it is 415 nm.

In yet a further embodiment of the method according to the invention, the fourth wavelength at which the absorbance not caused by bilirubin and hemoglobin and lipids is negligible is between 350 nm and 370 nm; preferably, it is 365 nm.

In a preferred embodiment of the method according to the invention, the extinction coefficient specific for lipids ($\epsilon_L$) is ascertained in advance by using the method according to the invention to determine natural lipid in native body fluid samples of known lipid content ascertained by chemical analysis ($L_1, L_2, \ldots L_n$). The advantage of this, with respect to the prior art-disclosed ascertainment of the extinction coefficient ($\epsilon_{Lipid}$), in which emulsions containing artificial lipid (e.g., Intralipid) are used, is that the later lipid determination has an increased accuracy.

"Measurement values" (A1; A2; A3, etc.) in the context of the present invention are absorbance measurement values which can be recorded using photometric measuring devices. A measurement value can be a dimensionless variable which indicates a wavelength-dependent measure of the opacity of a body fluid sample with respect to the passage of light beams in the visible, infrared and/or ultraviolet wavelength range. It may also be equally possible for absorbance measurement values to be specified with regard to a unit thickness of a measurement cell or cuvette in which body fluid samples are kept during the penetration of light beams for capturing intensity measurement values. In this case, the measurement values can have a dimension of [1/mm]. In any case, the indicated measurement values in the following embodiments are only of an exemplary nature and dependent on the measuring device, the sample characteristics and the sample composition. Hereinafter, absorbance measurement values will be equated in each case with absorption values, although it is clear to a person skilled in the art that while, in this consideration, diffraction, scattering and reflection contribute to the absorbance values, they are substantially negligible with respect to the absorption in the wavelength range considered.

"Theoretical absorbance values" ($E_H$, $E_B$, $E_{HBL}$, etc.) in the context of the present invention are not absorbance values that are actually measured, but calculated values.

"Lipids" in the context of the present application encompass in particular fats or triglycerides or triacylglycerols that occur in the human or animal organism.

In a preferred embodiment of the method according to the invention, the concentration of hemoglobin ($c_H$) and/or the concentration of bilirubin ($c_B$) is/are additionally determined.

This is done in case I.), i.e., if the deviation of the third theoretical absorbance value ($E_{HBL}$) from the fourth measurement value (A4), as ascertained in step j), does not exceed a predetermined threshold value, by outputting the approximation values for the hemoglobin concentration and the bilirubin concentration ($c_H$, $c_B$), as determined on the basis of the approximation curve ($L_0$) in steps g) and h), as actual hemoglobin and bilirubin concentrations.

In case II.), i.e., if the deviation of the third theoretical absorbance value ($E_{HBL}$) from the fourth measurement value (A4), as ascertained in step j), exceeds a predetermined threshold value, this is done by outputting the approximation values for the hemoglobin concentration and the bilirubin concentration ($c_H$, $c_B$), as determined on the basis of the corrected approximation curve ($L_k$) in steps g) and h), as actual hemoglobin and bilirubin concentrations.

In an advantageous embodiment, the predetermined threshold value for the deviation of the third theoretical absorbance value ($E_{HBL}$) from the fourth measurement value (A4) is 10 mAU.

In a further advantageous embodiment, the predetermined absorbance threshold value for the absorbance at the first wavelength is 950 mAU.

Advantageously, the transirradiation of the body fluid sample with light at a multiplicity of wavelengths is achieved using laser or light-emitting diodes or using a light source having various optical filters and the capture of the multiplicity of measurement values (A1; A2; A3; A4) is achieved using a photodetector, for example using a CCD sensor, a CMOS sensor, photosensors or similar devices suited to capturing the intensity of a light beam in a wavelength-dependent manner.

"Body fluid samples" in the context of the present invention can be all samples of biological origin which have a liquid consistency and comprise a multiplicity of biologically active substances in various concentrations. For example, body fluid samples can comprise blood serum, blood plasma, blood, urine, lymph, bile or similar fluids.

The present invention further provides an automatic analyzer comprising a measuring device designed to carry out method steps a) to e) of the method according to the invention and further comprising a calculation device, for example a processor, designed to carry out the remaining method steps for determining the concentration ($c_L$) of lipids as claimed in claim 1.

In one embodiment, the measuring device of the automatic analyzer comprises at least one light source and multiple optical filters for generating light of different wavelengths. In another embodiment, the measuring device comprises multiple light sources, preferably multiple light-emitting or laser diodes.

In a preferred embodiment, the measuring device of the automatic analyzer comprises at least four light sources, wherein the first light source emits light of a wavelength within the range between 600 nm and 660 nm, and the second light source emits light of a wavelength within the range between 440 nm and 480 nm, and the third light source emits light of a wavelength within the range between 400 nm and 440 nm, and the fourth light source emits light of a wavelength within the range between 350 nm and 370 nm.

In a particularly preferred embodiment, the measuring device of the automatic analyzer comprises at least four light sources, wherein the first light source emits light of a wavelength of 645 nm, and the second light source emits light of a wavelength of 470 nm, and the third light source emits light of a wavelength of 415 nm, and the fourth light source emits light of a wavelength of 365 nm.

Advantageously, the measuring device also comprises at least one photodetector, for example a CCD sensor, a CMOS sensor, photosensors or similar devices suited to capturing the intensity of a light beam in a wavelength-dependent manner.

Various exemplary embodiments and designs of the present invention will now be described in more detail with reference to the accompanying drawings.

BRIEF DESCRIPTION OF THE DRAWINGS

FIG. 1 shows a schematic representation of a graph containing the absorbance curve of a plasma sample. The absorbance curve (solid line) with the measurement values A1=$A_{645}$, A2=$A_{470}$, A3=$A_{415}$ and A4=$A_{365}$ reflects an exemplary schematic profile for the wavelength-dependent absorbance of human plasma with concentrations of hemoglobin, bilirubin and lipids, the respective absorbances of which overlap additively. The approximation curve $L_0$ (dotted line) for the absorbance of the lipids is calculated on the basis of the first measurement value $A1=A_{645}$ and the power function $E(\lambda)=p_0 \cdot \lambda^{q_0}$. The approximation curve $L_k$ (dashed line) is calculated and ultimately used for calculating the lipid concentration and the hemoglobin and bilirubin concentrations. The absorbance values of the measured plasma sample are comparatively low, and as a result, the approximation curve $L_0$ approximates the absorbance spectrum from below by iteration until it reaches the final approximation curve $L_k$.

DETAILED DESCRIPTION

Example a) Wavelengths

The method according to the invention was carried out in an automatic analyzer comprising a photometric arrangement having four laser diodes. Human plasma samples were transirradiated with light of the following wavelengths:

645 nm first wavelength at which the absorbance not caused by lipids is negligible;

470 nm second wavelength at which bilirubin has an absorbance maximum;

415 nm third wavelength at which hemoglobin has an absorbance maximum;

365 nm fourth wavelength at which the absorbance not caused by bilirubin and hemoglobin and lipids is negligible.

The above-mentioned four measurement values ($A2=A_{645}$, $A2=A_{470}$, $A3=A_{415}$ and $A4=A_{365}$) were recorded.

b) Lipid-Specific Extinction Coefficient

The lipid-specific extinction coefficient $\epsilon_{Lipid}$ was ascertained by measuring the absorbance spectrum using the above-mentioned wavelengths for 70 plasma samples of known lipid content ascertained by chemical analysis ($L_1$, $L_2$, ... $L_n$), calculating the power-function approximation curve ($L_0$) of the form $$E(\lambda)=p_0 \cdot \lambda^{q_0}$$

for the absorbance of the lipids using a predetermined exponent $q_0=-2.46$, and generating the value of the approximation curve ($L_0$) at the fourth wavelength ($E_{365}$) and the value of the approximation curve ($L_0$) at the first wavelength ($E_{645}$). The various absorbance values were calculated on the basis of the corrected approximation curve $L_k$ (see point c) below).

The difference between the values $E_{365}$ and $E_{645}$ divided by the lipid concentration yields the specific extinction coefficient for lipid. The mean and the median were generated across all measurements:

$$\epsilon_{Lipid} = \frac{1}{n}\sum_{i=1}^{n}\epsilon = \frac{\left[\frac{E_{1_{365}} - E_{1_{645}}}{L_1}\right] + \left[\frac{E_{2_{365}} - E_{2_{645}}}{L_2}\right] + \left[\frac{E_{n_{365}} - E_{n_{645}}}{L_n}\right]}{n}$$

The result is the lipid-specific extinction coefficient $\epsilon_{Lipid}=0.0010$ dL/mg.

c) Establishing the Power-Function Approximation Curve for the Absorbance of the Lipids and Calculating the Concentrations of Lipids and of Hemoglobin and Bilirubin The power-function approximation curve ($L_0$) of the form $$E(\lambda)=p_0 \cdot \lambda^{q_0}$$

for the absorbance of the lipids is calculated on the basis of the first measurement value ($A1=A_{645}$) by determining the factor $p_0$ at predetermined exponent $q_0$.

It is self-evident that solely the measurement value $A_{645}$ cannot yet be used for a determination of the two variables p and q. Therefore, the exponent $q_0$ can be generated on the basis of an estimation based on reference values. The exponent $q_0$ can thus be predetermined on the basis of empirical values. In the case of the determinations described here, an exponent $q_0=-2.46$ was predetermined. Since, at the first wavelength of 645 nm, the absorbance due to substances other than lipids can be ignored, it is possible to determine, at given exponent $q_0$, the coefficient $p_0$ via the measurement value $A_{645}$ at the first wavelength. The thus ascertained approximation curve having the parameters $p_0$ and $q_0$ can reflect a first approximation for the absorbance profile of the absorbance of lipids in the sample. Concerning this, it is possible, in the case of all wavelengths in which further measurement values have been captured, to calculate the particular share of the absorbance of the lipids.

The result of this is a first approximation curve $L_0$ which already provides a good approximation of the actual lipid absorbance. However, the approximation curve $L_0$, particularly within a blue or ultraviolet spectral range, may run flatter than the actual absorbance profile for lipids.

First approximation values for the concentrations of bilirubin ($c_B$) and hemoglobin ($c_H$) are then determined on the basis of the measurement values $A2=A_{470}$ and $A3=A_{415}$ at the wavelengths 470 nm and 415 nm:

$$c_B = \frac{A_{470} - c_H \cdot \epsilon_{H470} - E_{L470}}{\epsilon_{B470}}$$

$$c_H = \frac{A_{415} - c_B \cdot \epsilon_{B415} - E_{L415}}{\epsilon_{H415}}$$

where $\epsilon_{H470}$, $\epsilon_{H415}$, $\epsilon_{B470}$ and $\epsilon_{B415}$ are the respective extinction coefficients of bilirubin (B) and hemoglobin (H) at the wavelengths of the measurement values $A_{470}$ and $A_{415}$. In this connection, the extinction coefficients can be determined in advance by reference measurements, or be retrieved for the calculations from a storage device in which reference values have been stored.

The two concentrations $c_B$ and $c_H$ can be ascertained by solving the linear system of the two aforementioned equations, yielding the formula $$c_H = \frac{A_{470} - E_{LA70} - \frac{(A_{415} - E_{LA15}) \cdot \varepsilon_{B470}}{\varepsilon_{B415}}}{\varepsilon_{H470} - \frac{\varepsilon_{H415} \cdot \varepsilon_{B470}}{\varepsilon_{B415}}}$$

for the concentration of hemoglobin (H). Here, it is possible to determine the absorbance values for the lipids, $E_{L470}$ and $E_{L415}$, using the approximation curve $L_0$. The result is therefore a first approximation value for the concentration $c_H$ of hemoglobin. Said first approximation value for the concentration $c_H$ can then be used for determining the first approximation value for the concentration $c_B$ of bilirubin. This already yields first, good approximation values $c_H$, $c_B$ and $c_L$ for the concentrations of hemoglobin, bilirubin and lipids, which values were ascertained on the basis of the power function and the above-described linear system with the first approximation values for the parameters $p_0$ and $q_0$.

However, the approximation values can now be improved further iteratively, as will be described below. To this end, a theoretical absorbance value ($E_{HBL}$) for the fourth wavelength is determined on the basis of the sum of the theoretical absorbance values for hemoglobin ($E_H$) and bilirubin ($E_B$) and of the value of the approximation curve ($L_0$) at the fourth wavelength (365 nm), i.e., within a range in which a relatively high deviation of the actual lipid absorbance from the approximation curve is to be expected:

$$E_{HBL} = c_H \cdot \varepsilon_{H365} + c_B \cdot \varepsilon_{B365} + E_{L365}$$

The concentrations $c_H$ and $c_B$ were determined above; the value $E_{L365}$ ($E_{L4}$) is again yielded by the power function with the parameters $p_0$ and $q_0$.

Then, a comparison between the value $E_{HBL}$ and the actual measurement value $A4 = A_{365}$ at this wavelength is carried out in order for a deviation (DeltaE)

$$\Delta E = A_{365} - E_{HBL}$$

to be obtained. If the deviation $\Delta E$ (DeltaE) is greater than a predetermined threshold value, for example 10 mAU, it can be determined that the ascertained approximation curve $L_0$ for the concentrations of the lipids has not been ascertained sufficiently accurately enough. In this case, a correction of the approximation curve $L_0$ can be carried out in a further step. To this end, the calculated absorbance value $E_{L365}$ ($E_{L4}$), which describes the lipid share of absorbance at the wavelength 365 nm, can be corrected by a percentage of the deviation $\Delta E$. For example, half the value of the deviation $\Delta E$ can be added to the absorbance value $E_{L365}$ ($E_{L4}$). On the basis of the corrected absorbance value $E_{L365}$ ($E_{L4}$), it is then possible to determine a corrected approximation curve $L_k$ with the parameters $p_k$ and $q_k$:

$$q_k = \frac{\ln E_{L645} - \ln(E_{L365} + \Delta E/2)}{\ln \lambda_{645} - \ln \lambda_{365}}$$

$$p_k = \frac{E_{L365}}{\lambda_{365}^{q_k}}$$

The equations arise here by inserting the values of $E_{L365}$ and the corrected value $E_{L365} + \Delta E/2$ into the power function.

This means that the approximation curve $L_0$ can be corrected such that the measurement value $A1 = A_{645}$ at the wavelength of 645 nm continues to lie on the corrected approximation curve $L_k$, i.e., the measurement value $A_{645}$ is used as anchor point for the approximation curve.

In the next step, the various shares of absorbance of the lipids are then calculated on the basis of the corrected approximation curve $L_k$. The method is iterated until it is determined that the deviation falls short of the predetermined threshold value. The corrected approximation values for the concentrations of hemoglobin, bilirubin and lipids in the body fluid sample are then outputted.

Figure 1:
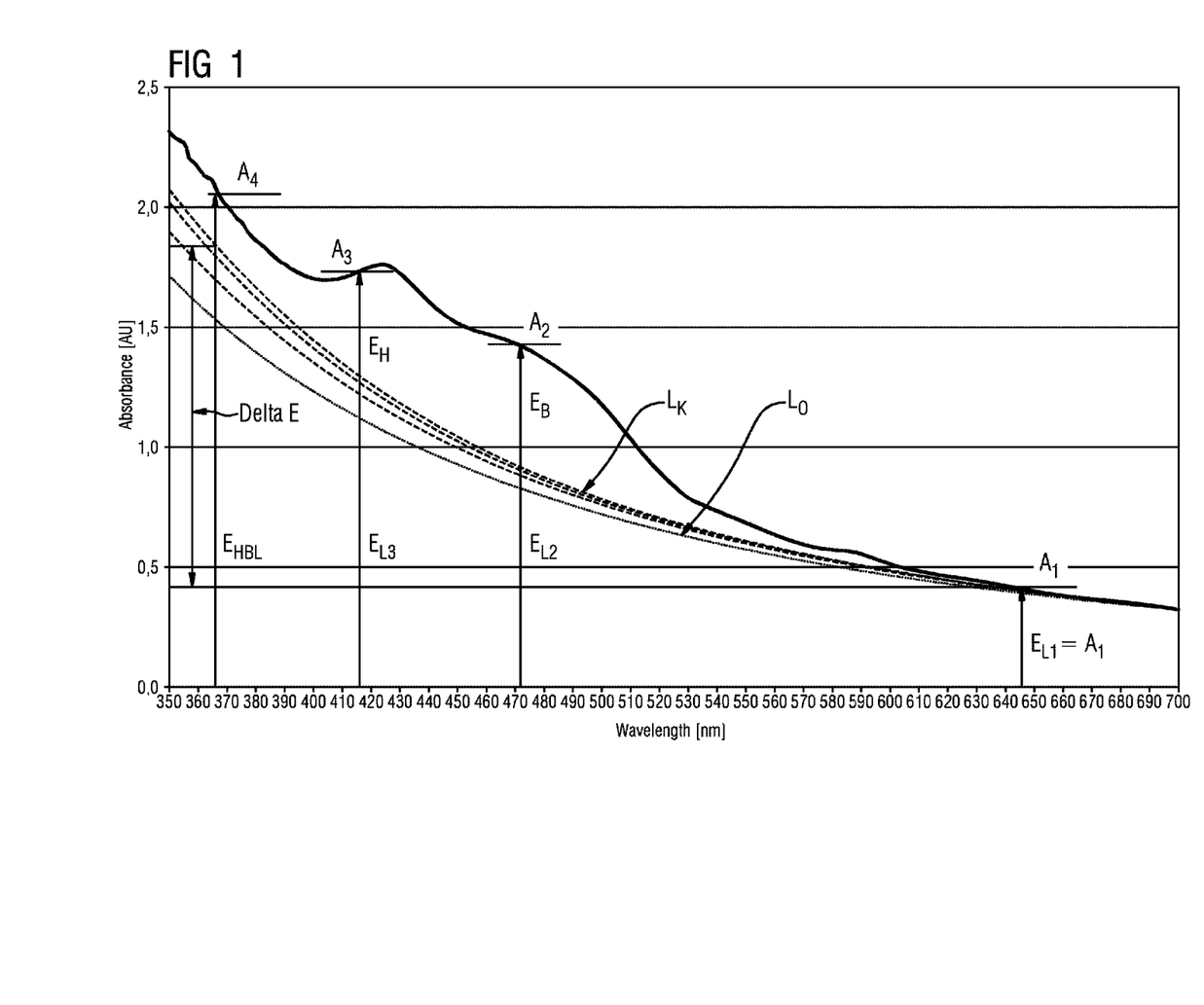
Figure 2:
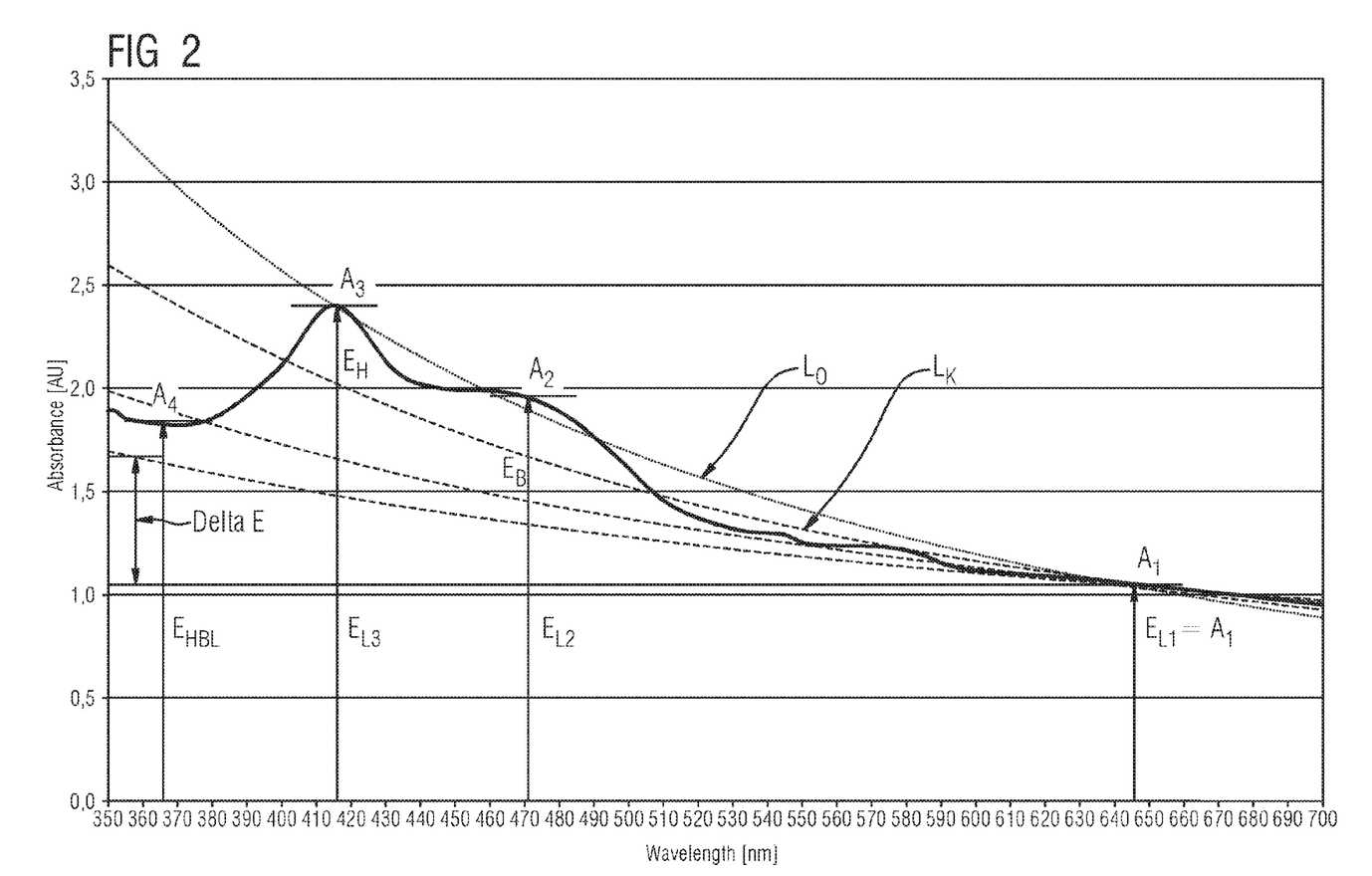
FIG. 2 shows, like FIG. 1, a schematic representation of a graph containing the absorbance curve of a plasma sample. In comparison with the sample from FIG. 1, the measured absorbance values in this case are comparatively high, and as a result, the approximation curve $L_0$ approximates the absorbance spectrum from above by iteration until it reaches the final approximation curve $L_k$.
Figure 3:
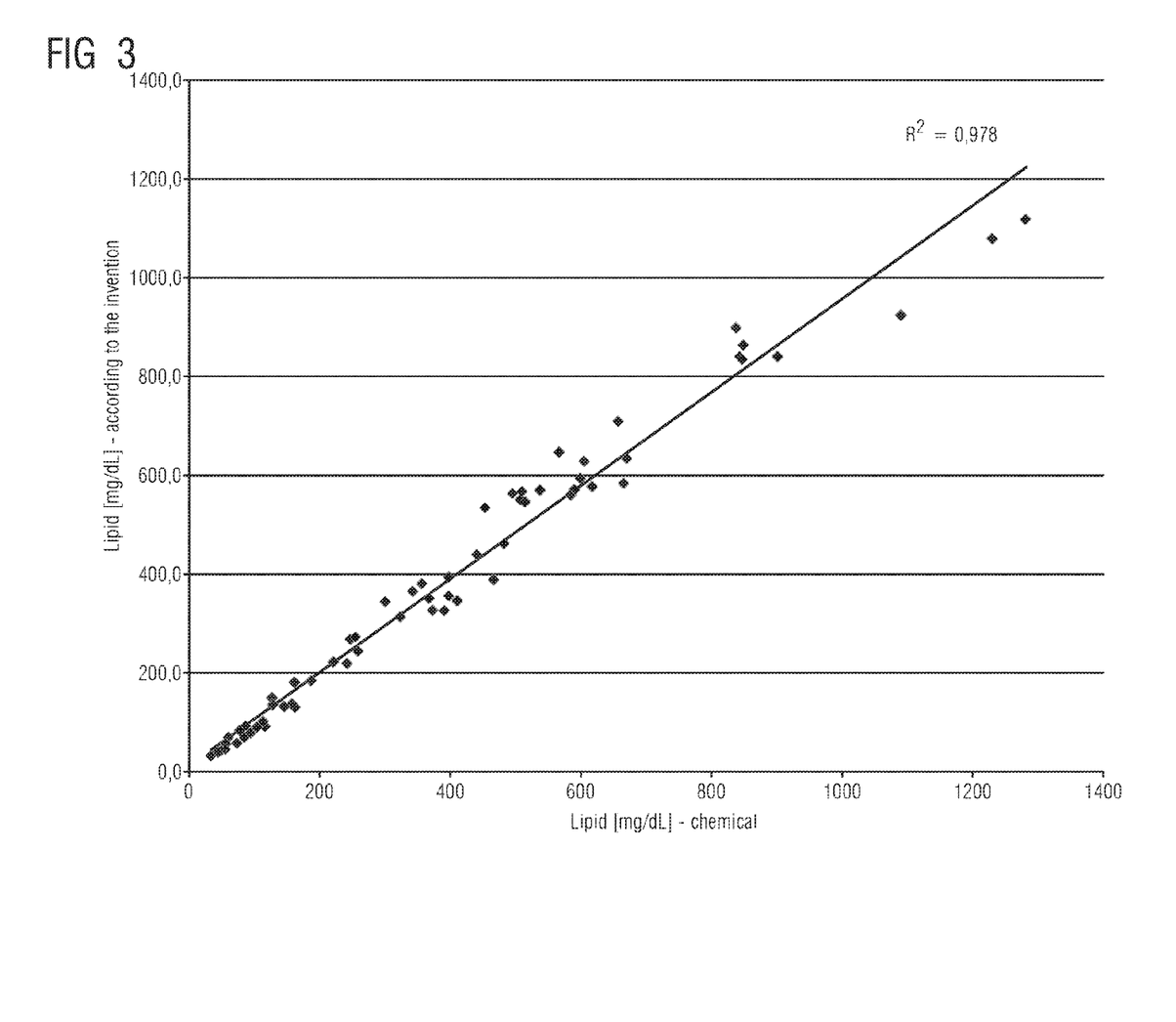
FIG. 3 shows a graph concerning the schematic representation of the comparison of the true lipid content ascertained by chemical analysis (X-axis) and the lipid content ascertained using the method according to the invention (Y-axis) for multiple human plasma samples. It is clear that the lipid content determined according to the invention does not deviate in any case by more than +/−20% from the true lipid content.

Using the described method, the lipid content in all the samples was determined with a deviation of not more than +/−20% from the true lipid content (see FIG. 3).

d) Determining the Lipid Content in Turbid Samples

Plasma samples which are frozen and thawed frequently exhibit a turbidity which can result in an elevated absorbance.

It has been found that, in contrast to the method known from WO 2013/010970 A1, it is possible to carry out a lipid determination independently of the turbidity using the method according to the invention.

The lipid content of a plasma sample (No. 2004657355) of known lipid concentration (667.7 mg/dL) was determined using the method according to the prior art from WO 2013/010970 A1 and the method according to the invention. The sample was then frozen, thawed after six months, and the lipid content was determined again. The total rise in absorbance of the thawed sample at the wavelengths used was 115%, i.e., the sample was more turbid after thawing than before freezing. The results are shown in Table 1. It can be seen from the table that, with the conventional method, the lipid content measured after thawing is more than twice that before freezing, but still deviates by more than 20% from the true lipid content, whereas with the method according to the invention, only a 5% deviation is measured after thawing with respect to before freezing. Moreover, the deviation from the true value of the lipid concentration is merely −4.7% or 0.4%, i.e., the method according to the invention is in principle also more accurate.

TABLE 1

Figure 4:
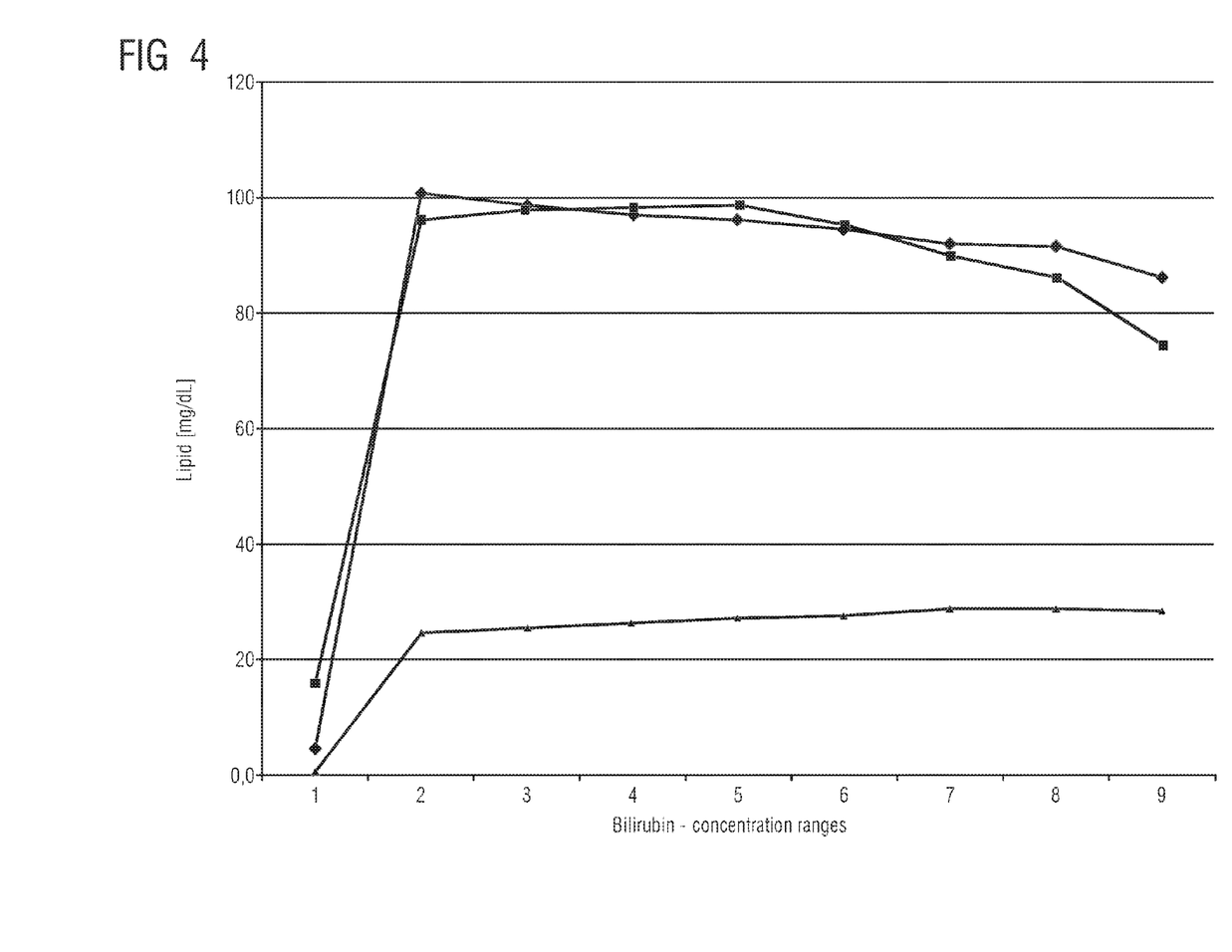
FIG. 4 shows a graph concerning the schematic representation of the comparison of the lipid determination (Y-axis) by means of chemical analysis (diamonds), by means of the method according to the prior art from WO 2013/010970 A1 (triangles) and by means of the method according to the invention (squares) in plasma samples having various bilirubin concentrations (X-axis). It is clear that the lipid content determined according to the invention substantially agrees with the lipid content determined chemically.

|  | Before freezing | After thawing |
| --- | --- | --- |
| Lipid determination according to prior art |  |  |
| Concentration | 227.8 mg/dL | 489.9 mg/dL |
| Relative deviation of the concentration from the true value (667.7 mg/dL) | −66% | −27% |
| Relative deviation of the concentration after thawing | — | +115% |
| Lipid determination according to invention |  |  |
| Concentration | 636.6 mg/dL | 670.6 mg/dL |
| Relative deviation of the concentration from the true value (667.7 mg/dL) | −4.7% | 0.4% |
| Relative deviation of the concentration after thawing | — | +5% | e) Determining the Lipid Content in the Presence of High Bilirubin Concentrations Various amounts of bilirubin were added to plasma samples so that 9 visually distinguishable concentration levels were obtained, and the lipid content was determined by chemical means, using the method according to the prior art from WO 2013/010970 A1 and using the method according to the invention. The results are shown in FIG. 4. It is clear from this that, in the presence of various bilirubin concentrations, the lipid determination according to the invention works virtually just as well as the determination by chemical means; the greatest deviation is merely 7% (concentration level 9).

f) Determining the Lipid Content in Highly Turbid Samples

Samples of very high turbidity, for example because of a very high lipid content (>500 mg/dL), have a high total absorbance. Therefore, in the case of some samples, a sufficiently accurate lipid determination is not possible using the method according to the invention, as described as before. The reason therefor is that, with the increase in lipid concentration, the absorbance spectrum of the sample firstly rises evenly, but then tips asymmetrically because the increase in absorbance is greater at high wavelengths than at lower wavelengths. As a result of this, the difference in absorbance between the first wavelength (645 nm) and the fourth wavelength (365 nm), which are used in the method according to the invention, is no longer large enough in order to be able to use the method to determine the lipid content with sufficient accuracy. Underdeterminations of up to −70% were observed.

However, this effect is correctable by means of an equalizing function. The equalizing function corrects the value of the corrected approximation curve ($L_k$) at the first wavelength ($E_{645}$). The equalizing function is ascertainable using a number of samples of known lipid concentration. By back-calculation of the concentration into the expected absorbance, it is possible to determine an equalizing function which allows calculation of the true lipid content.

Since turbidity is heavily dependent on absorbance at the wavelength 645 nm, the share of turbidity at 645 nm can be taken into account.

The calculation is formed as follows:

$$\text{Delta}E = E_{L365}(-0.7798 \cdot E_{L645} + 1.4626) \cdot E_{L645}|$$

Figure 5:
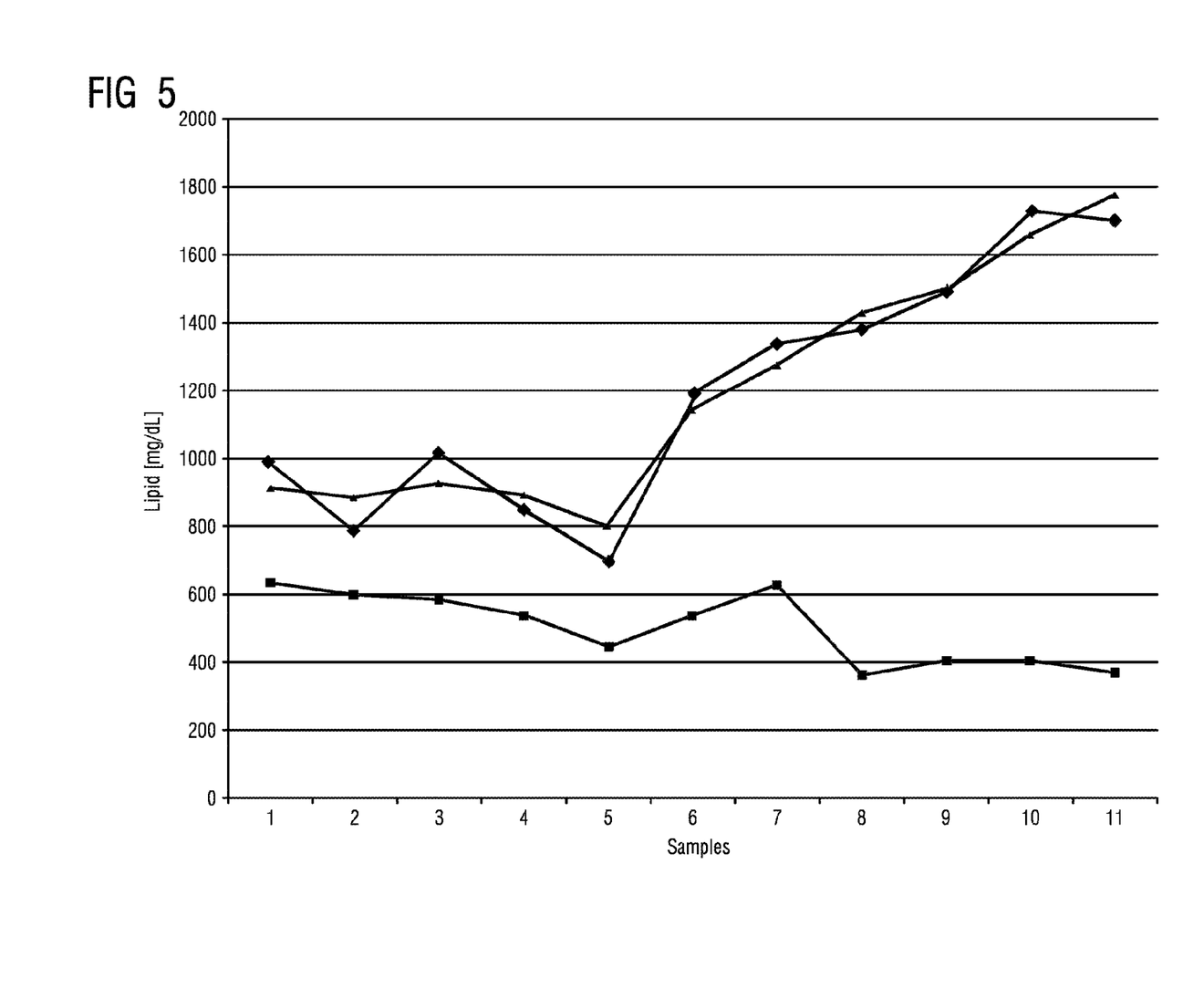
FIG. 5 shows a graph concerning the schematic representation of the comparison of the lipid determination (Y-axis) by means of chemical analysis (diamonds), by means of the method according to the invention without equalizing function (squares) and by means of the method according to the invention with equalizing function (triangles) in 11 plasma samples having high lipid concentrations (X-axis). It is clear that the determination according to the invention with equalizing function shows a good agreement with the chemical analysis.

The result of the application of this function to the first measurement value ($A1 = A_{645}$) of the samples and the ensuing division of the difference (Delta E) between the value of the corrected approximation curve ($L_k$) at the fourth wavelength (365 nm) and the value at the first wavelength (645 nm), as corrected by application of the equalizing function, by the extinction coefficient specific for lipids is that, even in the highly turbid samples, the lipid concentration can be determined with sufficient accuracy, with a deviation from the true value of less than +/−20%. FIG. 5 shows a comparison of the lipid determinations for 11 plasma samples having high lipid concentrations.

What is claimed is:

1. A method for determining the concentration of lipids in a body fluid sample, comprising the steps:
a) transirradiating the body fluid sample with light at a multiplicity of wavelengths;
b) capturing a first measurement value (A1) at a first wavelength at which the absorbance not caused by lipids is negligible;
c) capturing a second measurement value (A2) at a second wavelength at which bilirubin has an absorbance maximum;
d) capturing a third measurement value (A3) at a third wavelength at which hemoglobin has an absorbance maximum;
e) capturing a fourth measurement value (A4) at a fourth wavelength at which the absorbance not caused by bilirubin and hemoglobin and lipids is negligible;
f) calculating a power-function approximation curve ($L_0$) of the form $$E(\lambda) = p_0 \cdot \lambda^{q_0}$$

for the absorbance of the lipids on the basis of the first measurement value (A1) by determining the factor $p_0$ at predetermined exponent $q_0$;
g) determining an approximation value of the bilirubin concentration ($c_B$) on the basis of a first theoretical absorbance value ($E_B$) for bilirubin, corresponding to the difference between the second measurement value (A2) and the value of the approximation curve ($L_0$) at the second wavelength;
h) determining an approximation value of the hemoglobin concentration ($c_H$) on the basis of a second theoretical absorbance value ($E_H$) for hemoglobin, corresponding to the difference between the third measurement value (A3) and the value of the approximation curve ($L_0$) at the third wavelength;
i) determining a third theoretical absorbance value ($E_{HBL}$) for the fourth wavelength on the basis of the sum of the theoretical absorbance values for hemoglobin ($E_H$) and bilirubin ($E_B$) and the value of the approximation curve ($L_0$) at the fourth wavelength;
j) ascertaining a deviation of the third theoretical absorbance value ($E_{HBL}$) from the fourth measurement value (A4),
wherein:
I.—if the deviation ascertained in step j) does not exceed a predetermined threshold value—the concentration ($c_L$) of lipids is determined by generating the difference between the value of the approximation curve ($L_0$) at the fourth wavelength and the value of the approximation curve ($L_0$) at the first wavelength and dividing said difference by the extinction coefficient specific for lipids, or
II.—if the deviation ascertained in step j) exceeds a predetermined threshold value—a corrected approximation curve ($L_k$) for the absorbance of the lipids is calculated and steps g) to j) are repeated with the values of the corrected approximation curve ($L_k$) until the deviation reaches or falls short of the predetermined threshold value, and the concentration ($c_L$) of lipids is determined by
i.—if the first measurement value (A1) does not exceed a predetermined absorbance threshold value for the absorbance at the first wavelength—generating the difference between the value of the corrected approximation curve ($L_k$) at the fourth wavelength and the value of the approximation curve ($L_k$) at the first wavelength and dividing said difference by the extinction coefficient specific for lipids or
ii.—if the first measurement value (A1) exceeds a predetermined absorbance threshold value for the absorbance at the first wavelength and if the exponent $q_k$ of the corrected approximation curve is greater than −1—correcting the value of the corrected approximation curve ($L_k$) at the first wavelength by means of an equalizing function which relates the first measurement value (A1) to the value of the corrected approximation curve ($L_k$) at the first wavelength, and then generating the difference between the value of the corrected approximation curve ($L_k$) at the fourth wavelength and the value at the first wavelength, as corrected by application of the equalizing function, and dividing said difference by the extinction coefficient specific for lipids.

2. The method as claimed in claim 1, wherein the first wavelength is within the range between 600 nm and 660 nm, and the second wavelength is within the range between 440 nm and 480 nm, and the third wavelength is within the range between 400 nm and 440 nm, and the fourth wavelength is within the range between 350 nm and 370 nm.

3. The method as claimed in claim 2, wherein the first wavelength is 645 nm or the second wavelength is 470 nm or the third wavelength is 415 nm or the fourth wavelength is 365 nm.

4. The method as claimed in claim 1, wherein the concentration of hemoglobin ($c_H$) or the concentration of bilirubin ($c_B$) is additionally determined.

5. The method as claimed in claim 4, wherein, if the deviation ascertained in step j) does not exceed a predetermined threshold value, the concentrations ($c_H$, $c_B$) of hemoglobin and bilirubin are determined by outputting the approximation values of the hemoglobin concentration and the bilirubin concentration, as determined in steps g) and h), as concentrations ($c_H$, $c_B$) of hemoglobin and bilirubin.

6. The method as claimed in claim 3, wherein, if the deviation ascertained in step j) exceeds a predetermined threshold value, the concentrations ($c_H$, $c_B$) of hemoglobin and bilirubin are determined by outputting the approximation values of the hemoglobin concentration and the bilirubin concentration, as determined in steps g) and h) that are repeated with the values of the corrected approximation curve ($L_k$), as concentrations ($c_H$, $c_B$) of hemoglobin and bilirubin when the deviation reaches or falls short of the predetermined threshold value.

7. The method as claimed in claim 1, wherein the predetermined threshold value is 10 mAU.

8. The method as claimed in claim 1, wherein the predetermined absorbance threshold value for the absorbance at the first wavelength is 950 mAU.

9. The method as claimed in claim 1, wherein a transirradiation of the body fluid sample with light at a multiplicity of wavelengths is achieved using laser or light-emitting diodes or using a light source having various optical filters and wherein the capture of the multiplicity of measurement values (A1; A2; A3; A4) is achieved using a photodetector.

10. The method as claimed in claim 1, wherein the body fluid sample is serum or plasma.

11. An automatic analyzer comprising a measuring device designed to carry out method steps a) to e) as claimed in claim 1, characterized in that the analyzer further comprises a calculation device designed to carry out the remaining method steps for determining the concentration ($c_L$) of lipids as claimed in claim 1.

12. The automatic analyzer as claimed in claim 11, wherein the measuring device comprises at least one light source and multiple optical filters.

13. The automatic analyzer as claimed in claim 11, wherein the measuring device comprises multiple light sources, preferably multiple light-emitting or laser diodes.

14. The automatic analyzer as claimed in claim 13, wherein the measuring device comprises at least four light sources, wherein the first light source emits light of a wavelength within the range between 600 nm and 660 nm, and the second light source emits light of a wavelength within the range between 440 nm and 480 nm, and the third light source emits light of a wavelength within the range between 400 nm and 440 nm, and the fourth light source emits light of a wavelength within the range between 350 nm and 370 nm.

15. The automatic analyzer as claimed in claim 14, wherein the first light source emits light of a wavelength of 645 nm, and the second light source emits light of a wavelength of 470 nm, and the third light source emits light of a wavelength of 415 nm, and the fourth light source emits light of a wavelength of 365 nm.

16. The automatic analyzer as claimed in claim 11, wherein the measuring device comprises at least one photodetector.

* * * * *